United States Patent [19]

Lang et al.

[11] Patent Number: 5,067,532

[45] Date of Patent: Nov. 26, 1991

[54] APPARATUS FOR FILLING SELF-SEALING TUBES

[76] Inventors: John Lang, Shannon, County Sligo; Cormac Garvey, Boltown Hall, Kilskyre, Kells, County Meath, both of Ireland

[21] Appl. No.: 481,185

[22] Filed: Feb. 20, 1990

[30] Foreign Application Priority Data

Feb. 20, 1989 [IE] Ireland .................................. 2548/88

[51] Int. Cl.$^5$ .............................................. G01N 1/14
[52] U.S. Cl. ........................................ 141/329; 141/82; 141/130; 141/164; 141/165; 141/269; 141/270; 141/284; 269/270; 422/104
[58] Field of Search ............... 141/1, 329, 330, 130, 141/165, 168, 269, 270, 284, 369, 370, 372, 164, 171, 25-27, 97, 82; 269/25, 268, 270; 422/104

[56] References Cited

U.S. PATENT DOCUMENTS

| | | |
|---|---|---|
| 3,033,203 | 5/1962 | Barton . |
| 3,608,550 | 5/1969 | Stawski . |
| 3,807,467 | 4/1974 | Tascher et al. ................. 141/329 X |
| 4,041,994 | 8/1977 | Horwitz et al. ........................ 141/1 |
| 4,077,395 | 3/1978 | Woolner ......................... 141/130 X |
| 4,133,314 | 1/1979 | Bloom et al. . |
| 4,170,798 | 10/1979 | Krumdieck ..................... 141/130 X |
| 4,274,453 | 6/1981 | Lee .................... 73/864.84 |
| 4,342,341 | 8/1982 | Lee ........................................ 141/1 |
| 4,609,017 | 9/1986 | Coulter et al. ........................ 141/1 |
| 4,688,609 | 8/1987 | Diaz ...................................... 141/82 |
| 4,691,580 | 9/1987 | Fosslien ................................ 141/1 |
| 4,697,622 | 10/1987 | Switt et al. ............................ 141/1 |
| 4,703,781 | 11/1987 | Meyer et al. . |
| 4,865,090 | 9/1989 | Burolla et al. .................... 141/165 |

FOREIGN PATENT DOCUMENTS

| | | |
|---|---|---|
| 00049909 | 10/1978 | European Pat. Off. . |
| 2151729B2 | 10/1971 | Fed. Rep. of Germany . |
| 7406979 | 3/1974 | France . |
| 0633437 | 12/1949 | United Kingdom . |
| 1256523 | 5/1971 | United Kingdom . |
| 1386838 | 3/1975 | United Kingdom . |
| 1564009 | 4/1980 | United Kingdom . |
| 2095403 | 9/1982 | United Kingdom ................ 141/130 |

Primary Examiner—Ernest G. Cusick

[57] ABSTRACT

An apparatus includes a conveyor system for conveying tubes, having respective self-sealing closure members, sequentially to a station whereupon the conveyor system is temporarily halted. At the station, a clamping device having a clamp lowers to prevent movement of the tube. An arm moves in the direction of the tube to enable a hollow needle to penetrate the closure member of the tube. A metering pump enables a predetermined volume of a fluid, preferably liquid agar, to be introduced into the tube. Following release of the needle from the closure member, the conveyor systems moves to enable another tube to arrive at the station.

24 Claims, 3 Drawing Sheets

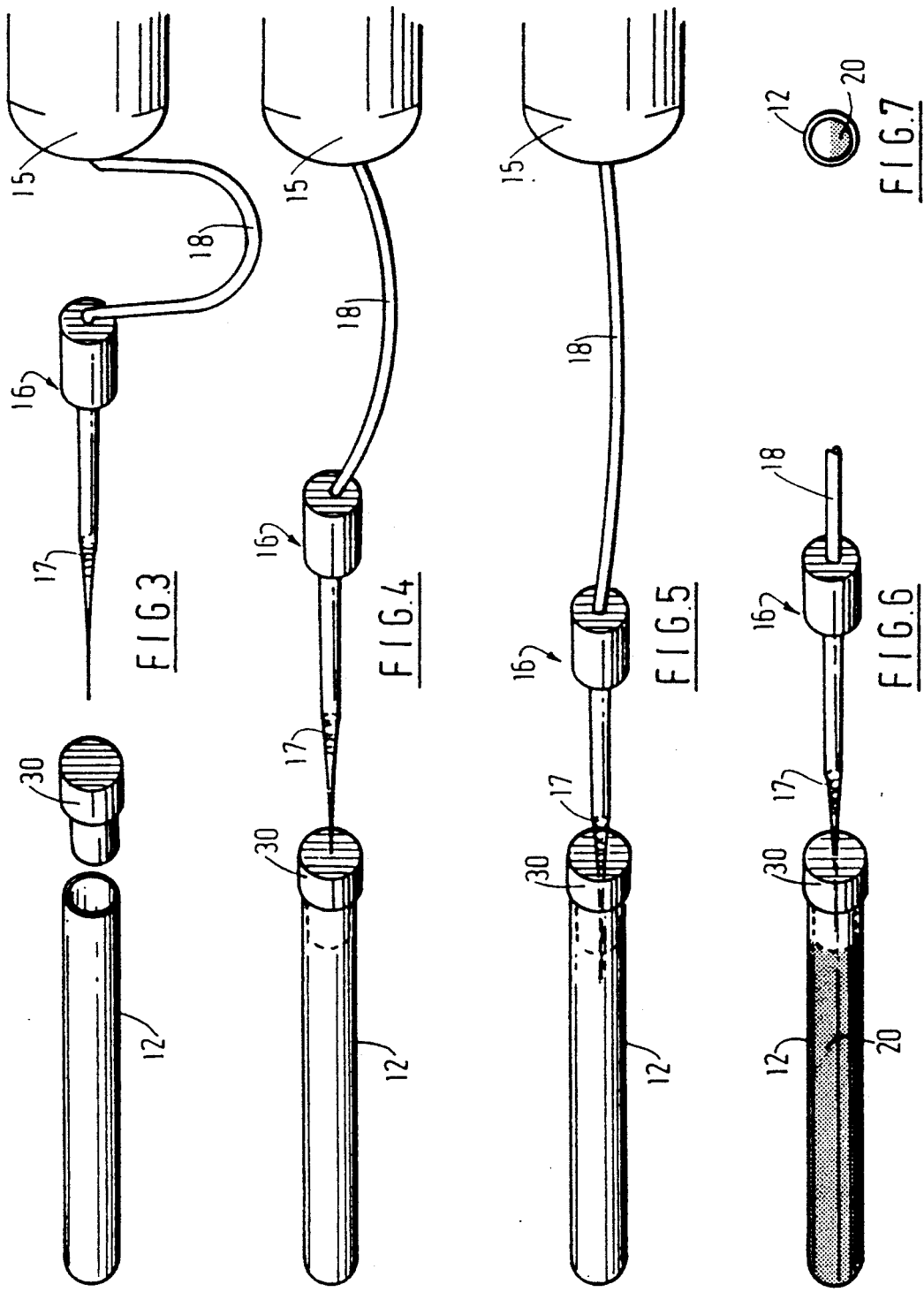

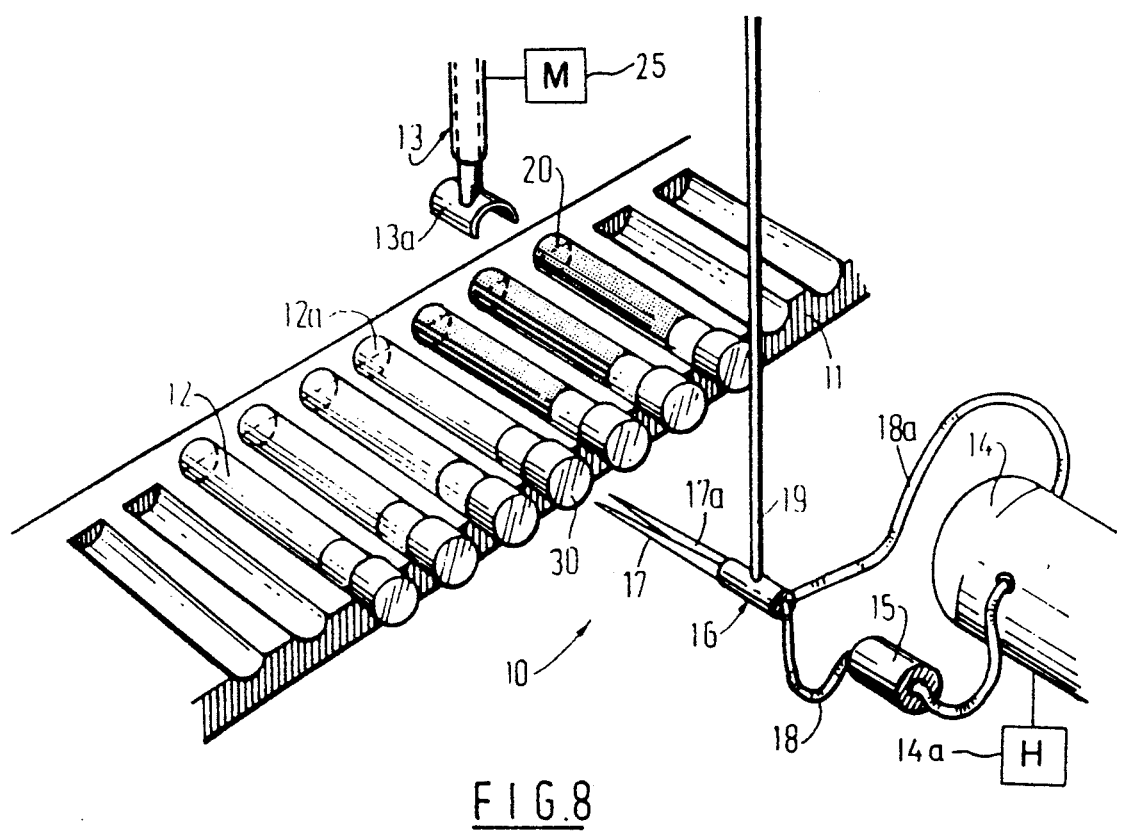
F I G.8

APPARATUS FOR FILLING SELF-SEALING TUBES this invention relates to an apparatus for filling tubes.

BACKGROUND OF THE INVENTION

VACUTAINER (registered trademark) tubes comprise a tube per se and a self-sealing stoppering or closure means. The closure means is made from a material which, on the one hand, seals the tube so as to prevent the interchange of liquids, gases or microscopic particles between the inside and the outside of the tube and on the other hand may be pierced by a syringe needle so as to admit a blood sample taken from a human or animal blood vessel. To assist in the sampling of the blood, the atmosphere of the VACUTAINER or self-sealing stoppered tube is at a reduced pressure relative to atmosphere. Once the needle as been removed from the closure means, the tube is again automatically sealed by virtue of the composition of the closure means.

OBJECTS AND SUMMARY OF THE INVENTION

It is an object of the present invention to utilize VACUTAINER tubes or self-sealing tubes in a new way for the purpose of holding a preset volume of a fluid initially in liquid form but which subsequently solidifies. It is a further object of the present invention to provide tubes containing the fluid which is sterile before, during and after placement thereof in the tube.

The invention, therefore, provides an apparatus for introducing a fluid into a tube having a self-sealing closure means which apparatus comprises means for releasably clamping the tube at a fluid injecting station; an injector device including a hollow needle; and means for enabling the needle to penetrate the closure means for introducing a charge of fluid into the tube and for enabling the needle to be withdrawn from the tube.

The invention also relates to a method of introducing a fluid into a tube having a self-sealing closure means which method comprises clamping the tube at a fluid injecting station; allowing a hollow needle to penetrate the closure means; introducing a charge of fluid into the tube via the needle; removing the needle from the tube; and releasing the tube.

The invention will be understood from the following description of a preferred embodiment thereof given by way of example only and with reference to the accompanying drawings in which:

BRIEF DESCRIPTION OF THE DRAWINGS

FIGS. 3 through 6 are perspective views of part of the apparatus of FIG. 1 in varying positions of use;

FIG. 7 is a cross-sectional view of a tube used with the apparatus of FIG. 1 of the drawings; and FIG. 8 is a perspective view of a second embodiment of an apparatus according to the invention.

DETAILED DESCRIPTION OF THE PREFERRED EMBODIMENTS

Figure 1:
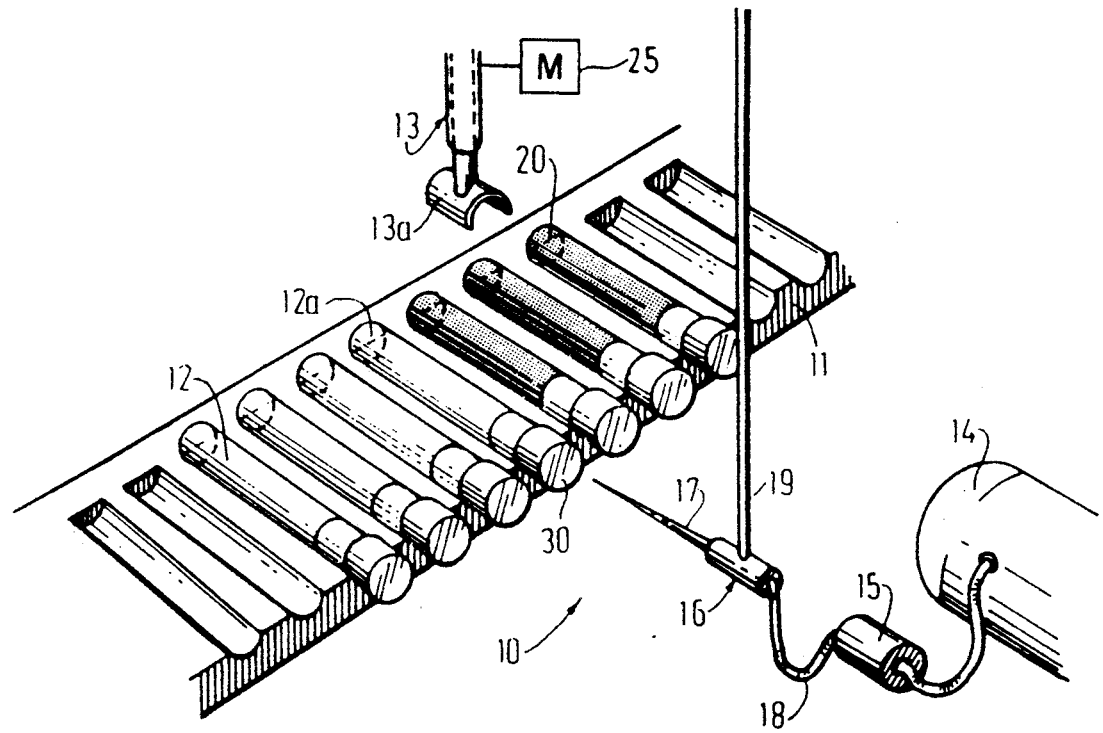
FIG. 1 is a perspective view of a first embodiment of an apparatus according to the invention in a first condition of use.
Figure 2:
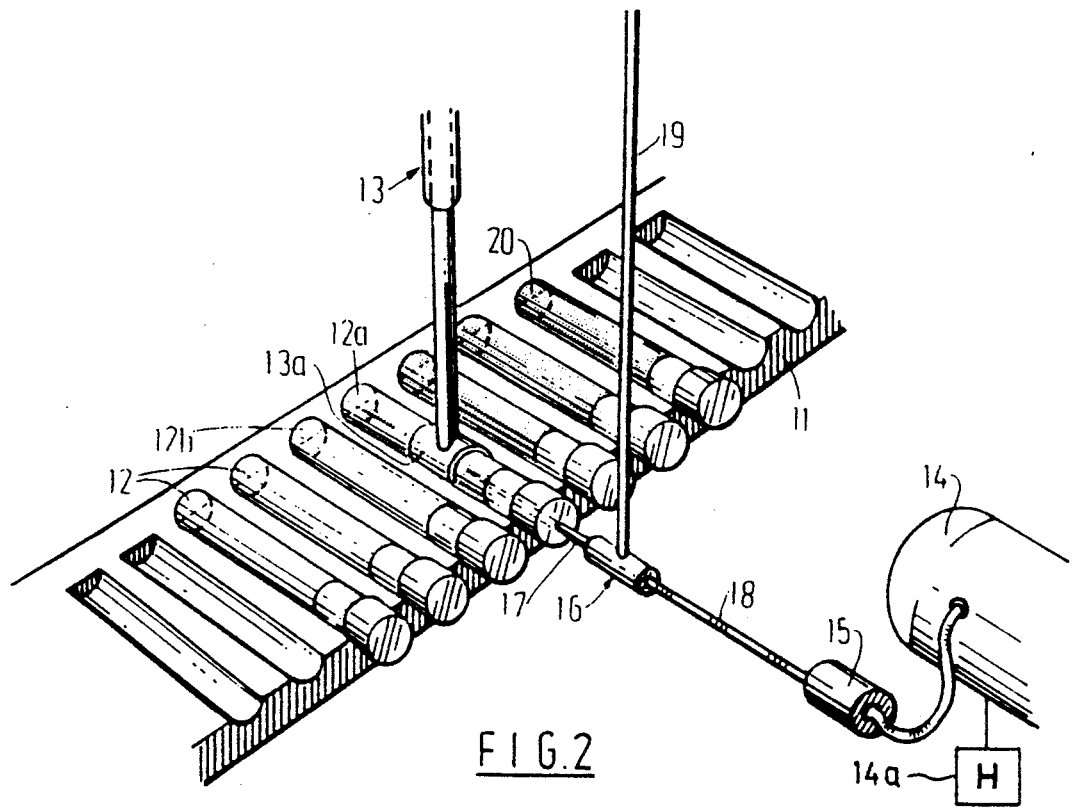
FIG. 2 is a perspective view of the apparatus of FIG. 1 in a second condition of use.

Referring now to the drawings, there is shown an apparatus 10 according to the invention which apparatus 10 comprises a conveyor system 11 for conveying tubes 12, each having a self-sealing closure means 30, sequentially to a station. The conveyor system 11 includes a base 13b having a shape conforming to one of the tubes 12. At the station, there is provided a clamping means 13 having a clamp 13a of substantially hemi-tubular construction for reciprocal movement from an elevated condition (FIG. 1) to a clamping position (FIG. 2).

The apparatus 10 further comprises a reservoir 14, a housing 15 and a needle support means 16. The needle support means 16, which includes a hollow needle 17, is connected to a metering means mounted in a housing 15 by a flexible pipe 18. Also attached to the needle support means 16 is an arm 19 adapted for reciprocal movement towards and away from the conveyor system 11 by a motor 25 or the like.

The metering means comprises a peristaltic pump of a known type which acts on the tbe 18 thereby enabling the delivery of a predetermined volume of fluid.

In use, a plurality of tubes 12 each having a respective closure means 30 is placed on the conveyor system 11 for sequential feeding to the station. When a tube 12a arrives at the station, the conveyor system 11 stops, the clamping means 13 lowers the clamp 13a to the clamping condition so as to prevent undue movement of the tube 12a. The arm 19 moves in the direction of the tube 12a to enable the hollow needle 17 to penetrate the closure means 30 of the tube 12a. Following penetration, the peristaltic pump in housing 15 is actuated to enable a predetermined volume of fluid to enter the tube 12a. Following the introduction of the required volume of fluid, the peristaltic pump is deactuated, and the arm 19 moves away from the tube 12a to release the needle 17 from the closure means 30. The clamping means 13 is elevated to release the tube 12a and the conveyor system 11 indexes to the right a distance sufficient to bring the next tube 12b to the station for the process to repeat.

The closure means 30 is made from a material which on the one hand seals the atmosphere of the tube 12 to prevent gaseous, liquid or microscopic particle from interchanging therethrough. However, the material may be penetrated by the needle 17. Following penetration and removal of the needle 17, the closure means 30 automatically reseals the tube 12.

The apparatus 10 according to the invention may be used under sterile conditions for the preparation of, for example, agar. In that event, the tubes 12 are evacuated to a pressure of about 45kPa and made sterile. The thermostable constituents of the agar are solublished and subjected to a temperature of about 120° C. at about 200kPa (2atm) for about 30 minutes in an autoclavable container which, if desired, can contain a batch of the tubes 12 previously evacuated and stoppered by respective closure means 30. The temperature of the constituents is lowered to about 50° C. and mixed with an appropriate quantity of sterile blood or other thermolabile substances. The mixture, which constitutes the agar, is placed in the previously sterile reservoir 14 and maintained at a temperature of about 50° C by a heater 14a. The tube 18, which connects the reservoir 14 with the needle 17, together with the needle 17 are also sterile.

Upon penetration of the needle 17 through the closure means 30, the negative pressure in the tube 12 assists in the placement of the agar in the tube 12. No venting of the tube 12 is required and hence there is no loss in the sterility of the contents of the tube 12. Following withdrawal of the needle 17 from the tube 12, a negative pressure of about 25kPa will still be present in the tube 12 relative to atmosphere. This partial vacuum can assist in the growth of microaerophilic bacteria.

Sterility can be checked in sample tubes of a batch by piercing the closure means 30 with a needle having a tube leading into water. Rapid respiration of the water will indicate that a partial vacuum was present in the tube.

The apparatus 10 according to the invention may be used with non-evacuated tubes 12 also under sterile conditions. To enable the peristaltic pump to operate in conjunction with non-evacuated stoppered tubes 12, the needle support means 16 includes a second hollow needle 17a in parallel, spaced apart relationship to the needle 17 as shown in FIG. 8 of the drawings. The second needle is connected via a tube 18a back to the reservoir 14. The needle 17a and associated tube 18a are also sterile. In use, both needes 17, 17a penetrate the closure means 30. The second needle 17a enables venting of the tube 30 without loss of sterility. If desired, the reservoir 15 may be vented to the atmosphere via an opening having a suitable filter therein such as a 0.22 micron filter.

The volume of fluid dispensed into the tube 12a is about 4ml with an adjustable flow rate depending on the velocity of the liquid. The volume is adjustable by virtue of the peristaltic pump.

The apparatus 10 enables quick, easy and sterile filling of tubes 12 with a suitable fluid for subsequent use.

In particular, and in regard to FIG. 7 of the drawings, the injection of the agar 20 into the tubes 12 while in the horizontal position and subsequently maintaining the tubes 12 in the horizontal condition until the agar 20 has set will provide an agar surface area of a significant size when compared with the placing of agar in tubes 12 held in a vertical condition. It will further be appreciated that the tube 12 need not necessarily be placed in the horizontal condition when in use for bacteriological culture analysis but, with regard to the solidified agar 20 may be placed in the vertical position.

The apparatus 10 may, therefore, be used in a non-sterile but relatively clean area. The apparatus is particularly useful where particle-free loading areas would be difficult or uneconomic to implement.

The invention is not limited by or to the specific embodiment described which can undergo considerable variation without departing from the scope of the invention.

We claim:

1. An apparatus for introducing a fluid into a tube having a self-sealing closure means, said apparatus comprising:
   a base;
   clamping means having a substantially hemi-tubular construction for releasably clamping the tube against the base at a fluid injecting station and for releasably maintaining the tube in a substantially horizontal position;
   injector means including a first hollow injector needle selectively engageable with said closure means;
   means for enabling the needle to penetrate the closure means thereby introducing a charge of liquid into the tube and for enabling the needle to be withdrawn from the tube; and
   means for raising and lowering the clamping means relative to the tube so that in a first position of use, the clamping means is in engagement with the tube so as to bias the tube gently but firmly downwards against the base and in a second position of use the clamping means is out of engagement with the tube.

2. The apparatus as claimed in claim 1, wherein the hollow injector needle includes a reservoir for the fluid and metering means for pumping the fluid.

3. The apparatus as claimed in claim 2, wherein the metering means includes a peristaltic pump.

4. The apparatus as claimed in claim 2, wherein the fluid is sterile, and the tube, the reservoir and the injector needle for conveying the fluid from the reservoir into the tube provide a sterile pathway for the fluid.

5. The apparatus as claimed in claim 1, wherein the base comprises a conveyor apparatus for enabling a plurality of tubes to be fed sequentially to and from the fluid injecting station, said conveyor apparatus is operatively associated with the clamping means so that when the clamping means is in the first position of use, the conveyor apparatus is stationary.

6. The apparatus as claimed in claim 1, wherein the fluid is liquid agar.

7. The apparatus as claimed in claim 1, further including heating means for maintaining the agar at the temperature of about 50° C.

8. The apparatus as claimed in claim 1, wherein the tube is an evacuated tube.

9. The apparatus as claimed in claim 1, wherein the tube is a non-evacuated tube.

10. The apparatus as claimed in claim 9, wherein the injector means includes a second hollow needle in a parallel spaced apart relationship relative to the first needle, which second needle enables venting of the tube during fluid introduction into the tube.

11. The apparatus as claimed in claim 1, wherein the fluid is sterile and the tube and the hollow injector needle for conveying the fluid into the tube provide a sterile pathway for the fluid.

12. An apparatus for introducing a fluid into a tube having a self-sealing closure means, said apparatus comprising:
    a base;
    clamping means for releasably clamping the tube against the base at a fluid injection station;
    a first hollow injector needle selectively engageable with said closure means; and
    means for enabling the first needle to penetrate the closure means for introducing a charge of fluid into the tube and for enabling the needle to be withdrawn from the tube;
    wherein the base comprises a conveyor apparatus for enabling a plurality of tubes to be fed sequentially to and from the station, said conveyor being operatively associated with the clamping means so that when the clamping means is in the first position of use, the conveyor apparatus is stationary.

13. The apparatus as claimed in claim 12, wherein the clamping means is adapted for maintaining the tube in a substantially horizontal position.

14. The apparatus as claimed in claim 12, wherein the clamping means is of substantially hemi-tubular construction and comprises means for raising and lowering the clamp relative to the tube so that in a first position of use, the clamping means is in engagement with the tube so as to bias the tube gently but firmly downwards against the base and in a second position of use the clamping means is out of engagement with the tube.

15. The apparatus as claimed in claim 12, wherein the means for metering comprises a peristaltic pump.

16. The apparatus as claimed in claim 12, wherein the fluid is liquid agar.

17. The apparatus as claimed in claim 16, further including heating means for maintaining the agar at a temperature of about 50° 1 C.

18. The apparatus as claimed in claim 12, wherein the tube is evacuated.

19. The apparatus as claimed in claim 12, wherein the tube is non-evacuated.

20. The apparatus as claimed in claim 19, wherein the injector means includes a second hollow needle in a parallel spaced apart relationship relative to the first needle, said second needle enabling venting of the tube during fluid introduction into the tube.

21. The apparatus as claimed in claim 12, and further comprising a reservoir for the fluid.

22. The apparatus as claimed in claim 12, and further comprising means for metering the fluid.

23. The apparatus as claimed in claim 12, wherein the fluid is sterile and the tube and the first needle for conveying the fluid into the tube provide a sterile pathway for the fluid.

24. The apparatus as claimed in claim 21 wherein the fluid is sterile and the tube, the resevoir and the first needle for conveying the fluid from the reservoir into the tube provide a sterile pathway for the fluid.

* * * * *